United States Patent [19]
Bruns et al.

[11] 3,993,697
[45] Nov. 23, 1976

[54] ODORIFEROUS CYCLOALKYL ACETALS

[75] Inventors: Klaus Bruns, Krefeld-Traar; Peter Meins, Mettmann, both of Germany

[73] Assignee: Henkel & Cie G.m.b.H., Dusseldorf-Holthausen, Germany

[22] Filed: May 29, 1975

[21] Appl. No.: 581,783

[30] Foreign Application Priority Data

June 7, 1974 Germany ........................... 2427500

[52] U.S. Cl. ............................. 260/611 R; 252/522
[51] Int. Cl.[2] ......................................... C07C 43/18
[58] Field of Search ................................. 260/611 R

[56] References Cited

UNITED STATES PATENTS

| | | | |
|---|---|---|---|
| 3,024,284 | 3/1962 | Howard et al. | 260/611 R |
| 3,061,649 | 10/1962 | Erickson et al. | 260/611 R |
| 3,876,561 | 4/1975 | Naegeli | 260/611 R X |

OTHER PUBLICATIONS

Shostakouskii et al., Jour. Applied Chem., vol. 8 (Nov. 1958), p. ii–478.

*Primary Examiner*—Bernard Helfin
*Attorney, Agent, or Firm*—Hammond & Littell

[57] ABSTRACT

An odoriferous acetal having the formula

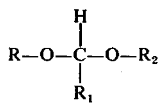

wherein R is a cycloalkyl having from 8 to 12 carbon atoms, $R_1$ is a member selected from the group consisting of hydrogen and methyl, and $R_2$ is a member selected from the group consisting of methyl, ethyl, propyl, isopropyl, allyl and propargyl. These compounds have a woody amber odor and are useful in the preparation of scents.

16 Claims, No Drawings

ODORIFEROUS CYCLOALKYL ACETALS

OBJECTS OF THE INVENTION

An object of the present invention is the development of an odoriferous acetal having the formula

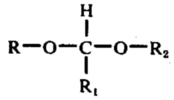

wherein R is a cycloalkyl having from 8 to 12 carbon atoms, $R_1$ is a member selected from the group consisting of hydrogen and methyl, and $R_2$ is a member selected from the group consisting of methyl, ethyl, propyl, isopropyl, allyl and propargyl.

Another object of the present invention is the development of a process for the preparation of the above odoriferous acetal which consists of the steps of reacting a cycloalkanol having the formula

R—OH wherein R is a cycloalkyl having from 8 to 12 carbon atoms with an excess of an aldehyde having the formula $R_1$—CHO wherein $R_1$ is a member selected from the group consisting of hydrogen and methyl and an excess of hydrogen chloride in an inert organic solvent under conditions whereby water is removed as it is produced, reacting the resulting chloroalkoxy-cycloalkane having the formula

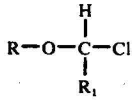

wherein R and $R_1$ have the above assigned values, with an alkali metal alcoholate having the formula $MeOR_2$ wherein Me is an alkali metal and $R_2$ is a member selected from the group consisting of methyl, ethyl, propyl, isopropyl, allyl and propargyl, and recovering said odoriferous acetal.

A yet further object of the present invention is the development of odoriferous compositions of various odor giving compounds containing from 1 to 50% by weight of the above odoriferous acetal.

These and other objects of the invention will become more apparent as the description thereof proceeds.

DESCRIPTION OF THE INVENTION

The present invention provides compounds having the formula

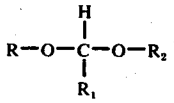

wherein R represents a cycloaliphatic group, preferably a cycloalkyl group, having 8 to 12 carbon atoms, $R_1$ represents hydrogen or a methyl group and $R_2$ represents a methyl, ethyl, propyl, isopropyl, allyl or propargyl group. These compounds are excellent odoriferous substances having a woody amber quality of scent.

The present invention also provides a process for the production of a compound of the present invention which comprises reacting a cycloalkanol having the formula R—OH with an aldehyde having the formula $R_1$—CHO and hydrogen chloride in an organic solvent with removal of water formed, to give the appropriate cycloalkyl-chloralkyl-ether or chloroalkoxycycloalkane having the formula

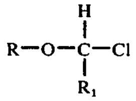

which in the second stage is then reacted with an alkoxide having the formula $MeOR_2$, in which Me preferably represents an alkali metal, particularly sodium, to give the odoriferous acetal having the formula

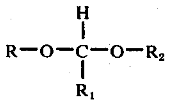

In these formulae R, $R_1$ and $R_2$ are as defined above.

Suitable cycloaliphatic starting alkanols are cyclooctanol, cyclononanol, cyclodecanol, cycloundecanol and cyclododecanol. Of these, cyclooctanol and cyclododecanol are of the greatest importance in view of their availability.

The aldehydes which are to be reacted with the abovementioned cycloalkanols are formaldehyde and acetaldehyde, formaldehyde being of greater importance because the compounds derived therefrom have a stronger smell and are more suitable as odoriferous substances.

The alcoholates to be used in the second step of the process of the present invention particularly the sodium alcoholates, are obtained from methanol, ethanol, propanol, isopropanol, allyl alcohol and propargyl alcohol. Of these, methanol and ethanol are of the greatest importance since products having the most intensive smell are obtained when they are used.

Accordingly, the following constitute new odoriferous substances of the invention falling under the formula: formaldehyde-methyl-cyclooctyl-acetal, formaldehyde-methyl-cyclononyl-acetal, formaldehyde-methyl-cyclodecyl-acetal, formaldehyde-methyl-cycloundecyl-acetal, formaldehyde-methyl-cyclododecyl-acetal, formaldehyde-ethyl-cyclooctyl-acetal, formaldehyde-ethyl-cyclononyl-acetal, formaldehyde-ethyl-cyclodecyl-acetal, formaldehyde-ethyl-cycloundecyl-acetal, formaldehyde-ethyl-cyclododecyl-acetal, formaldehyde-propyl-cyclooctyl-acetal, formaldehyde-propyl-cyclononyl-acetyl, formaldehyde-propyl-cyclodecyl-acetal, formaldehyde-propyl-cycloundecyl-acetal, formaldehyde-propyl-cyclododecyl-acetal, formaldehyde-isopropyl-cyclooctyl-acetal, formaldehyde-isopropyl-cyclononyl-acetal, formaldehyde-isopropyl-cyclodecyl-acetal, formaldehyde-isopropyl-cycloundecyl-acetal, formaldehyde-isopropyl-cyclododecyl-acetal, formaldehyde-allyl-cyclo-octyl-acetal, formaldehyde-allyl-cyclononyl-acetal, formaldehyde-allyl-cyclodecyl-acetal, formaldehyde-allyl-cyclo-undecyl-acetal, formaldehyde-allyl-cyclododecyl-acetal, formaldehyde-propargyl-cyclooctyl-acetal, formaldehyde-propargyl-cyclononyl-acetal, formaldehyde-propargyl-cyclodecyl-acetal, formaldehyde-propargyl-cycloundecyl-acetal, formaldehyde-propargyl-cyclododecyl-acetal, acetaldehyde-methyl-cyclooctyl-acetal, acetaldehyde-methyl-cyclononyl-acetal, acetaldehyde-methyl-cyclodecyl-acetal, acetaldehyde-methyl-cycloundecyl-acetal, acetaldehyde-methyl-cyclododecyl-acetal, acetaldehyde-ethyl-cyclooctyl-acetal, acetaldehyde-ethyl-cyclononyl-acetal, acetaldehyde-ethyl-cyclodecyl-acetal, acetaldehyde-ethyl-cycloundecyl-acetal, acetaldehyde-ethyl-cyclododecyl-acetal, acetaldehyde-propyl-cyclooctyl-acetal, acetaldehyde-propyl-cyclononyl-acetal, acetaldehyde-propyl-cyclodecyl-acetal, acetaldehyde-propyl-cycloundecyl-acetal, acetaldehyde-propyl-cyclododecyl-acetal, acetaldehyde-isopropyl-cyclooctyl-acetal, acetaldehyde-isopropyl-cyclononyl-acetal, acetaldehyde-isopropyl-cyclodecyl-acetal, acetaldehyde-isopropyl-cycloundecyl-acetal, acetaldehyde-isopropyl-cyclododecyl-acetal, acetaldehyde-allyl-cyclooctyl-acetal, acetaldehyde-allyl-cyclononyl-acetal, acetaldehyde-allyl-cyclodecyl-acetal, acetaldehyde-allyl-cycloundecyl-acetal, acetaldehyde-allyl-cyclododecyl-acetal, acetaldehyde-propargyl-cyclooctyl-acetal, acetaldehyde-propargyl-cyclononyl-acetal, acetaldehyde-propargyl-cyclodecyl-acetal, acetaldehyde-propargyl-cycloundecyl-acetal and acetaldehyde-propargyl-cyclododecyl-acetal.

Of the above-mentioned compounds, which are suitable as new odoriferous substances, the products formaldehyde-methyl-cyclooctyl-acetal, formaldehyde-methyl-cyclododecyl-acetal, formaldehyde-ethyl-cyclooctyl-acetal and formaldehyde-ethyl-cyclododecyl-acetal are being the most important, and formaldehyde-methyl-cyclooctyl-acetal and formaldehyde-methyl-cyclododecyl-acetal are the most significant.

The odoriferous acetals of the invention are produced by reacting the cycloalkanol with the aldehyde and hydrogen chloride under conditions where the water formed is excluded from the reaction, and thereafter reacting the chloroalkoxy-cycloalkane with an alkali metal alcoholate. The first step is preferably conducted with an excess of the aldehyde and hydrogen chloride to avoid formation of a gem.-acetal. The amount of excess of the aldehyde is immaterial although amounts of from 2 to 15 mols per mol of cycloalkanol are often employed. The reaction is conducted in an inert organic solvent liquid at the temperatures employed, such as chlorinated hydrocarbon solvents and aromatic hydrocarbon solvents, at temperatures of from 10° C down to the freezing point of the solvent mixture. Excess hydrogen chloride is introduced, preferably in a gas stream at such a rate that the upper temperature limit is not exceeded, for a time sufficient for at least the stoichiometric amount of HCl to be reacted. The reaction is conducted under anhydrous conditions and the water produced by the reaction is removed as it is produced. Preferably the water is removed by conducting the reaction in the presence of an inert, anhydrous, inorganic salt which combines with water to form a crystalline salt with water of crystallization, such as sodium sulfate.

The second step of the reaction is preferably conducted with the solution of the reaction product of the first step after separation of the solid inorganic salt combined with water. This solution is added to the alkali metal alcoholate, preferably in solution in the same alcohol at a low temperature, of from 25° C down to the freezing point of the solvent mixture. Preferably, the solution is added to the alkali metal alcoholate solution at a rate whereby the reaction temperature does not exceed 20° C. The alkali metal alcoholate is employed in excess of the stoichiometric amount.

After the addition to the alkali metal alcoholate has been completed, the reaction is continued at an elevated temperature of from 30° C up to the reflux temperature for a further period of 0.25 to 5 hours. The sodium chloride formed is separated and the odoriferous acetal is obtained after distilling off the solvents.

The new odoriferous substances of the invention are marked by a particularly intensive and lingering woody amber type of scent of high quality and richness. Other advantageous properties of the new odoriferous acetals are their good combination with other odoriferous substances to give novel nuances of scent, and their special adhering capacity.

The new odoriferous acetals of the invention can be mixed with other odoriferous substances in the most diverse quantity ratios to give new odoriferous substance compositions. However, the proportion of the new odoriferous acetals in the odoriferous substance compositions will generally range from 1 to 50% by weight, based on the entire composition. Such compositions can be used as they are as perfume, or to perfume cosmetics, such as creams, lotions, toilet water, aerosols, toilet soaps etc. However, they can also be used, as is also possible in the case of the actual new compounds, to improve the smell of technical products, such as washing and cleaning agents, disinfectants, agents for treating textiles, etc.

The following examples are intended to describe the subject matter of the invention in greater detail without, however, restricting it to said examples.

The production of the new odoriferous acetals is to be described first of all.

EXAMPLE 1

Formaldehyde-methyl-cyclododecyl-acetal 368 gm of cyclododecanol (2.0 mols), 250 gm of anhydrous sodium sulfate and 66,0 gm of paraformaldehyde were dispersed in 600 ml of xylene and the mixture was cooled to a temperature of −20° C. While the mixture was stirred energetically, as strong a flow as possible of hydrogen chlorine was introduced, the speed at which it was introduced being controlled such that the reaction temperature did not exceed +5° C. After approximately one hour the speed of introduction was decreased and subsequent reaction was effected while hydrogen chloride was bubbled through gently. Water-jet vacuum was then applied gradually during energetic stirring in order to remove surplus hydrogen chloride. When the highest water-jet vacuum had been achieved, the mixture was heated to 30° C over a period of one hour, and subsequent stirring was effected at this temperature for a further hour. The sodium sulfate was then drawn off by vacuum filtration and the solution of the chloromethoxy-cyclododecane thus obtained could be used for the next reaction without special processing.

The solution of the chloromethoxy-cyclododecane was added during stirring and in the course of 1 to 2 hours to 400 gm of a 33% sodium methoxide solution in methanol, which solution had been cooled to a temperature of −20° C at a rate such that the temperature did not exceed 20° C. Subsequent to this addition, stirring was effected for a further hour at 40° to 50° C. The majority of the sodium chloride which had separated out was dissolved and separated off by stirring briefly with 700 ml of cold water. The organic phase was then washed with 100 ml of a 20% sodium chloride solution. The separated organic solution was subsequently freed of solvent and the formaldehyde-methyl-cyclododecyl-acetal which was obtained was distilled at 0.01 torr. 433 gm i.e. 95% of theory, was obtained. The formaldehyde-methyl-cyclododecyl-acetal is a colorless liquid and has the following characteristic data:

Boiling point at 0.01 Torr = 86° C Density $d_4^{20}$ = 0.9463

Refractive index $n_D^{20}$ = 1.4695

IR(Film): 1370, 1342, 1142, 1098, 1060, 1030/cm (C—O—$CH_2$—O—C)

NMR ($CCl_4$): Δ 4.56 (S) 2H (O—$CH_2$—O); 3.33 (S) 3H ($OCH_3$)

MS: M+ = 228, m/e = 45 ($CH_3$—O—$CH_2^+$)

The chloromethoxy-cyclododecane obtained as intermediate product is a colorless liquid having the following characteristic data:

Boiling point at 0.5 Torr = 110° C

Density $d_4^{20}$ = 1.0142

Refractive index: $n_D^{20}$ = 1.4892

IR (film): 1120/cm (C—O—C); 645/cm (C—Cl)

NMR ($CDCl_3$): δ 5.6 (S) 2H (C—O—$CH_2$—Cl)

MS: $M^+$ = 233, $M^+$−36 (HCl), $M^+$−66 ($HOCH_2Cl$-elimination → cyclododecene$^+$)

EXAMPLE 2

Formaldehyde-ethyl-cyclododecyl-acetal

The product was obtained by reacting chloromethoxy-cyclododecane with sodium ethoxide and is a colorless liquid having the following characteristic data;

Boiling point at a 0.001 Torr = 94° C

Refractive index $n_D^{20}$ = 1.4665

NMR ($CCl_4$): δ 4.7 (S) 2H (O—$CH_2$—O); 3.6 (q) 2H/J=7 Hz (O—$CH_2$—C); 1.2 (t) 3H/J = 7 Hz (O—C—$CH_3$)

MS: $M^+$ = 242, m/e = 59 ($CH_3$—$CH_2$—O—$CH_2^+$)

EXAMPLE 3

Formaldehyde-propyl-cyclododecyl-acetal

The product was obtained by reacting chloromethoxy-cyclododecane with sodium propoxide, and is a colorless liquid having the following characteristic data;

Boiling point at 0.01 Torr = 97° C

Refractive index $n_D^{20}$ = 1.4677

EXAMPLE 4

Formaldehyde-isopropyl-cyclododecyl-acetal

The compound, which is a colorless liquid, was obtained by reacting chloromethoxy-cyclododecane with sodium isopropoxide.

Boiling point at 0.01 Torr = 94° C

Refractive index $n_D^{20}$ = 1.4657

EXAMPLE 5

Formaldehyde-allyl-cyclododecyl-acetal

The compound was produced by reacting chloromethoxycyclododecane with the sodium compound of allyl alcohol, and is a colorless liquid having the following characteristic data:

Boiling point at 0.01 Torr = 107° C

Refractive index $n_D^{20}$ = 1.4760

EXAMPLE 6

Formaldehyde-propargyl-cyclododecyl-acetal

The product, which is a colorless liquid, was obtained by reacting chloromethoxy-cyclododecane with the sodium compound of propargyl alcohol, and has the following characteristic data:

Boiling point at 0.005 Torr + 104° C

Refractive index $n_D^{20}$ = 1.4821

EXAMPLE 7

Formaldehyde-methyl-cyclooctyl-acetal

In accordance with the process given in Example 1, the chloromethoxy-cyclooctane was first of all produced from cyclooctanol, paraformaldehyde and hydrogen chloride, and was then reacted in the second stage with sodium methoxide to give formaldehyde-methyl-cyclooctyl-acetal, a colorless liquid having the following characteristic data:

Boiling point at 0.4 Torr = 75° C

Density $d_4^{20}$ = 0.9557

Refractive index $n_D^{20}$ = 1.4570

IR (film): 1378, 1360, 1150, 1090, 1045/cm (C—O—$CH_2$—O—C)

NMR ($CCl_4$): δ 4.6 (S) 2H (O—$CH_2$—O); 3.35 (S) 3H ($OCH_3$)

MS: $M^+$ = 172,$M^+$ − 32 ($CH_3OH$), $M^+$ − 61 ($CH_3$—O—$CH_2$—O) m/e = 45 ($CH_3$—O—$CH_2^+$)

EXAMPLE 8

Formaldehyde-ethyl-cyclooctyl-acetal

The product was obtained by reacting chloromethoxy-cyclooctane with sodium ethoxide and is a colorless liquid having the following characteristic data:

Boiling point at 0.4 Torr = 82° C

Density $d_D^{20}$ = 0.9399

Refractive index $n_D^{20}$ = 1.4548

NMR: ($CCl_4$): δ 4.7 (S) 2H (O—$CH_2$—O): 3.6 (q) 2 H/J = 7 Hz (O—$CH_2$—C) 1.2 (t) 3 H/J = 7 Hz (O—C—$CH_3$)

MS: $M^+$ = 186, $M^+$ − 29 ($CH_2$—$CH_3$), $M^+$ − 46 ($CH_3$—$CH_2$—O) $M^+$ − 59 ($CH_3$—$CH_2$—O—$CH_2$), m/e = 59 ($CH_3$—$CH_2$—O—$CH_2^+$)

EXAMPLE 9

Formaldehyde-allyl-cyclooctyl-acetal

The compound was produced by reacting chloromethoxycyclooctane with the sodium compound of allyl alcohol. It is a colorless liquid having the following characteristic data:

Boiling point at 0.2 Torr = 101.5° C

Refractive index $n_D^{20}$ = 1.4685

EXAMPLE 10

Formaldehyde-propargyl-cyclooctyl-acetal

The product, a colorless liquid, was obtained by reacting chloromethoxy-cyclooctane with the sodium compound of propargyl alcohol and has the following characteristic data:

Boiling point at 0.1 Torr = 104° C

Refractive index $n_D^{20} = 1.4752$

All the compounds mentioned in the above Examples have an persistant woody scent, which makes them suitable for the production of the most diverse odoriferous substance compositions. Such compositions can be used to perfume the most diverse products, such as cosmetics, washing agents, soaps, but also technical products, in concentrations of approx. 0.05 to 2% by weight. Several Examples of odoriferous substance compositions containing compounds of the invention are given hereinafter.

EXAMPLE 11

| Woody scent base composition | parts by weight |
|---|---|
| Formaldehyde-methyl-cyclododecyl-acetal | 500 |
| Oryclon | 100 |
| Vetiveryl acetate | 100 |
| Sandlewood oil | 100 |
| Isoraldein 70 | 50 |
| Guaiyl acetate | 50 |
| Coumarin | 50 |
| Phenyl ethyl alcohol | 50 |

EXAMPLE 12

| Woody scent base composition | parts by weight |
|---|---|
| Formaldehyde-methyl-cyclooctyl-acetal | 140 |
| Bergamot oil | 250 |
| Bulgarian rose oil | 50 |
| Sandlewood oil | 40 |
| Vetiver oil | 110 |
| Cedar oil | 50 |
| Cinnamyl acetate | 40 |
| Coumarin | 70 |
| Methylionone | 150 |
| Peru balsam | 40 |
| Benzyl acetate | 60 |

EXAMPLE 13

| Woody quality substance composition | parts by weight |
|---|---|
| Formaldehyde-ethyl-cyclododecyl-acetal | 250 |
| Sandlewood oil | 355 |
| Bergamot oil | 100 |
| Vetiver oil | 50 |
| Coumarin | 50 |
| Rose oil | 50 |
| Amyl salicylate | 75 |
| Heliotrepin | 50 |
| Xylene musk | 20 |

EXAMPLE 14

| Imaginative perfuming composition | parts by weight |
|---|---|
| Formaldehyde-propargyl-cyclododecyl-acetal | 340 |
| Geranium oil | 100 |
| Lavender oil | 100 |
| Cedar oil | 100 |

-continued

| Imaginative perfuming composition | parts by weight |
|---|---|
| Anisaldehyde | 150 |
| Butylphenyl acetate | 50 |
| Hydroxy-citronellal | 50 |
| Methyl naphthyl ketone | 50 |
| Benzyl acetate | 40 |
| Xylene musk | 20 |

EXAMPLE 15

| Imaginative perfuming composition with a hay-like quality | parts by weight |
|---|---|
| Formaldehyde-allyl-cyclooctyl-acetal | 30 |
| Bergamot oil | 250 |
| Lavender oil | 200 |
| Hydroxy-citronellal | 200 |
| Linalool | 50 |
| Methyl salicylate | 50 |
| Ylang-ylang oil | 50 |
| Coumarin | 60 |
| Tonka abs. | 30 |
| Oak moss | 20 |
| Ketone musk | 20 |
| Vetiver oil | 10 |
| Patchouli oil | 10 |
| Benzyl acetate | 10 |
| Vanillin | 10 |

In the above-listed odoriferous substance compositions it is also possible for the stated acetals to be replaced by other compounds of the invention, thus producing shifts in the scent nuances.

The proceeding specific embodiments are illustrative of the practice of the invention. It is to be understood however, that other expedients known to those skilled in the art or disclosed herein may be employed without departing from the spirit of the invention or the scope of the appended claims.

We claim:

1. An odoriferous acetal having the formula

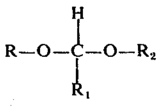

wherein R is a cycloalkyl having from 8 to 12 carbon atoms, $R_1$ is a member selected from the group consisting of hydrogen and methyl, and $R_2$ is a member selected from the group consisting of methyl, ethyl, propyl, isopropyl, allyl and propargyl.

2. The odoriferous acetal of claim 1 wherein R is cyclooctyl.

3. The odoriferous acetal of claim 1 wherein R is cyclododecyl.

4. The odoriferous acetal of claim 1 wherein $R_1$ is hydrogen.

5. The odoriferous acetal of claim 1 wherein $R_2$ is methyl.

6. The odoriferous acetal of claim 1 wherein $R_2$ is ethyl.

7. The odoriferous acetal of claim 1 wherein R is cyclododecyl, $R_1$ is hydrogen and $R_2$ is methyl.

8. The odoriferous acetal of claim 1 wherein R is cyclododecyl, $R_1$ is hydrogen and $R_2$ is ethyl.

9. The odoriferous acetal of claim 1 wherein R is cyclododecyl, $R_1$ is hydrogen and $R_2$ is propyl.

10. The odoriferous acetal of claim 1 wherein R is cyclododecyl, $R_1$ is hydrogen and $R_2$ is isopropyl.

11. The odoriferous acetal of claim 1 wherein R is cyclododecyl, $R_1$ is hydrogen and $R_2$ is allyl.

12. The odoriferous acetal of claim 1 wherein R is cyclododecyl, $R_1$ is hydrogen and $R_2$ is propargyl.

13. The odoriferous acetal of claim 1 wherein R is cyclooctyl, $R_1$ is hydrogen and $R_2$ is methyl.

14. The odoriferous acetal of claim 1 wherein R is cyclooctyl, $R_1$ is hydrogen and $R_2$ is ethyl.

15. The odoriferous acetal of claim 1 wherein R is cyclooctyl, $R_1$ is hydrogen and $R_2$ is allyl.

16. The odoriferous acetal of claim 1 wherein R is cyclooctyl, $R_1$ is hydrogen and $R_2$ is propargyl.

* * * * *